US012708428B2

(12) United States Patent
Szabo

(10) Patent No.: US 12,708,428 B2
(45) Date of Patent: Aug. 18, 2026

(54) BIPOLAR SCISSOR VESSEL SEALER FORCE LIMITING MECHANISM

(71) Applicant: ConMed Corporation, Largo, FL (US)

(72) Inventor: Aaron Szabo, Swanton, OH (US)

(73) Assignee: ConMed Corporation, Largo, FL (US)

( * ) Notice: Subject to any disclaimer, the term of this patent is extended or adjusted under 35 U.S.C. 154(b) by 172 days.

(21) Appl. No.: 18/682,233

(22) PCT Filed: Oct. 28, 2022

(86) PCT No.: PCT/US2022/048215
§ 371 (c)(1),
(2) Date: Feb. 8, 2024

(87) PCT Pub. No.: WO2023/076592
PCT Pub. Date: May 4, 2023

(65) Prior Publication Data

US 2024/0358430 A1 Oct. 31, 2024

Related U.S. Application Data

(60) Provisional application No. 63/272,892, filed on Oct. 28, 2021.

(51) Int. Cl.
*A61B 18/12* (2006.01)
*A61B 18/14* (2006.01)
*A61B 18/00* (2006.01)

(52) U.S. Cl.
CPC *A61B 18/1445* (2013.01); *A61B 2018/00184* (2013.01); *A61B 2018/00404* (2013.01);
(Continued)

(58) Field of Classification Search
CPC ...... A61B 18/1445; A61B 2018/00184; A61B 2018/00404; A61B 2018/00604;
(Continued)

(56) References Cited

U.S. PATENT DOCUMENTS 7,234,377 B2 * 6/2007 Wolfson .................... B25B 7/02 81/418
7,267,677 B2 * 9/2007 Johnson ............. A61B 18/1445 606/171

(Continued)

FOREIGN PATENT DOCUMENTS

WO 2021021803 A1 2/2021
WO 2022098738 A1 5/2022

OTHER PUBLICATIONS

International Search Report and Written Opinion of PCT/US2022/048215, filed Oct. 28, 2022. pp. 1-9. Mailing date of Search Report, Feb. 20, 2023.

*Primary Examiner* — Daniel W Fowler

(74) *Attorney, Agent, or Firm* — Bond, Schoeneck & King, PLLC; David L. Nocilly

(57) ABSTRACT

A scissor style vessel sealer having a first shaft interconnected to a first jaw by a pivot plate that pivotally couples the first shaft to the first jaw by the pivot and also by a spring that is secured at one end to the first shaft and an opposing end to the pivot plate at a location offset from the pivot and a second shaft connected to a second jaw and pivotally coupled to the first jaw by the pivot. The first shaft and the second shaft are then pivotable from a jaws open position to a jaw closed position. Any further application of force results in the first shaft pivoting relative to the first jaw so that the additional force is not transmitted to the jaws. The first shaft pivoting relative to the first jaw may actuate a button associated with the second shaft.

20 Claims, 5 Drawing Sheets

(52) U.S. Cl.
CPC ............... *A61B 2018/00601* (2013.01); *A61B 2018/0063* (2013.01)

(58) Field of Classification Search
CPC ...... A61B 2018/0063; A61B 2018/126; A61B 2018/1455; A61B 2018/146
See application file for complete search history.

(56) References Cited

U.S. PATENT DOCUMENTS

| | | | | | |
|---|---|---|---|---|---|
| 10,144,117 | B2* | 12/2018 | Khristyuchenko | B25B 7/10 | |
| 2004/0193199 | A1* | 9/2004 | Hashiguchi | A61B 17/320092 | 606/169 |
| 2008/0215048 | A1* | 9/2008 | Hafner | A61B 18/1442 | 606/42 |
| 2013/0018411 | A1* | 1/2013 | Collings | A61B 17/285 | 606/205 |
| 2015/0164526 | A1* | 6/2015 | Bernhardt | B26B 13/12 | 606/205 |
| 2016/0058498 | A1* | 3/2016 | Goodman | A61B 18/1442 | 606/42 |
| 2016/0175033 | A1 | 6/2016 | Le | | |
| 2017/0105788 | A1* | 4/2017 | Boudreaux | A61B 17/2841 | |
| 2017/0196620 | A1* | 7/2017 | Jadhav | A61B 18/1445 | |
| 2020/0015881 | A1* | 1/2020 | Cummings | A61B 18/1442 | |
| 2020/0246064 | A1 | 8/2020 | Gutti | | |
| 2020/0383719 | A1* | 12/2020 | Sims | A61B 18/1442 | |
| 2020/0405374 | A1* | 12/2020 | Sims | A61B 17/2816 | |
| 2020/0405376 | A1* | 12/2020 | Sims | A61B 18/085 | |

* cited by examiner

BIPOLAR SCISSOR VESSEL SEALER FORCE LIMITING MECHANISM

BACKGROUND

1. Field

The present application related to bipolar scissor vessel sealers and, more specifically, to an approach for limiting the amount of force applied by a user.

2. Description of the Related Art

Electrosurgical vessel sealers are used for the occlusion of blood vessels and halting of bleeding during surgical procedures. The electrodes of the vessel sealer are carried by a pair of opposing jaws and interconnected to an electrosurgical generator that can selectively supply radiofrequency (RF) energy to the electrodes. A user may close the jaws around a vessel to be sealed by squeezing a scissoring assembly associated with a user handles at one end and the jaws at the other. The vessel may then be sealed by supplying the RF energy to the clamped vessel. A moveable blade may be additionally incorporated into the jaws for cutting of the sealed blood vessel along an intermediate portion of the seal created by the energized electrodes in response to user activation of a second trigger.

BRIEF SUMMARY

Users of conventional vessel sealers, such as scissor style vessel sealers, may often continue to apply a force to the scissors after the jaws have completely closes. This over-application of force can result in breakage of the device. As a result, the inventors recognize that there is a need in the art for an approach that can limit the amount of force that a user can apply to the jaws via the scissored handles. In one aspect, a scissor style vessel sealer has a first shaft interconnected to a first jaw by a pivot plate that pivotally couples the first shaft to the first jaw by the pivot and also by a spring that is secured at one end to the first shaft and an opposing end to the pivot plate at a location offset from the pivot and a second shaft connected to a second jaw and pivotally coupled to the first jaw by the pivot. The first shaft and the second shaft are pivotable about the pivot between a first position where the first jaw and the second jaw are open and a second position where the first jaw and the second jaw are closed. The first shaft and the second shaft are pivotable about the pivot to a third position where the first jaw and the second jaw are closed and the first shaft has pivoted relative to the first jaw. The first shaft is in contact with the second shaft in the third position. The second shaft may include a button positioned to be actuated by the first shaft when the first shaft and the second shaft are in the third position. The button may be is coupled to a linkage that provides feedback to a user that the scissor style vessel sealer is in the third position. The button may be coupled to a linkage that triggers energization of the first jaw and the second jaw. The button may be coupled to a linkage that moves a knife blade between the first jaw and the second jaw.

In other aspect, the scissor style vessel sealer has a first shaft interconnected to a first jaw by a pivot and a second shaft connected to a second jaw and pivotally coupled to the first jaw by the pivot. The first shaft is free to pivot relative to the first jaw about the pivot in response a predetermined amount of force applied to the first shaft. The first shaft and the second shaft are pivotable about the pivot between a first position where the first jaw and the second jaw are open and a second position where the first jaw and the second jaw are closed. The first shaft and the second shaft are pivotable about the pivot to a third position where the first jaw and the second jaw are closed and the first shaft has pivoted relative to the first jaw. The scissor style vessel sealer may further have a spring interconnected between the first shaft and the first jaw that provides a biasing force coupling the first shaft to the first jaw. The predetermined amount of force applied to the first shaft overcomes the biasing force of the spring such that the first shaft will pivot about the pivot relative to the first jaw. The spring may be is secured at one end to the first shaft and an opposing end to a pivot plate that is pivotally connected to the first shaft by the pivot. The pivot plate is fixed to the first jaw.

In a further aspect, a method of providing force limiting to a scissor style vessel sealer includes providing a first shaft interconnected to a first jaw by a pivot plate that pivotally couples the first shaft to the first jaw by the pivot and also by a spring that is secured at one end to the first shaft and an opposing end to the pivot plate at a location offset from the pivot and providing a second shaft connected to a second jaw and pivotally coupled to the first jaw by the pivot. The method may further comprise the step of applying a force to the first shaft and the second shaft so that the first shaft and the second pivot about the pivot from a first position where the first jaw and the second jaw are open to a second position where the first jaw and the second jaw are closed. The method may additionally comprise the step of continuing to apply the force to the first shaft and the second shaft so that the first shaft pivots relative to the first jaw. The pivoting of the first shaft relative to the first jaw may cause the first shaft to contact the second shaft. The contacting of the first shaft to the second shaft may actuate a button.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION

Figure 1:
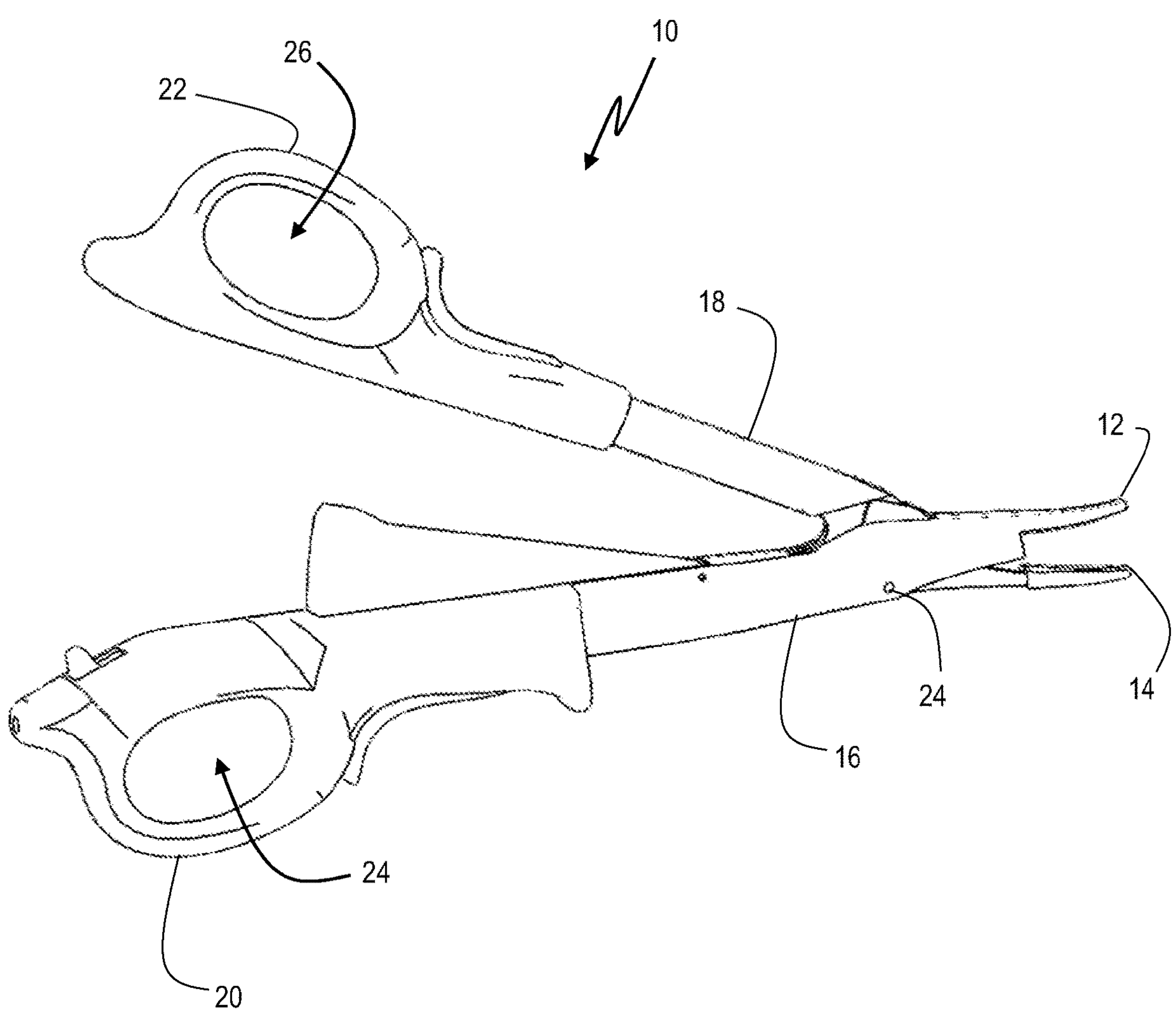
FIG. 1 is a side view of a scissor style vessel sealer having a force limiting mechanism according to the present invention in the jaws open position.
Figure 2:
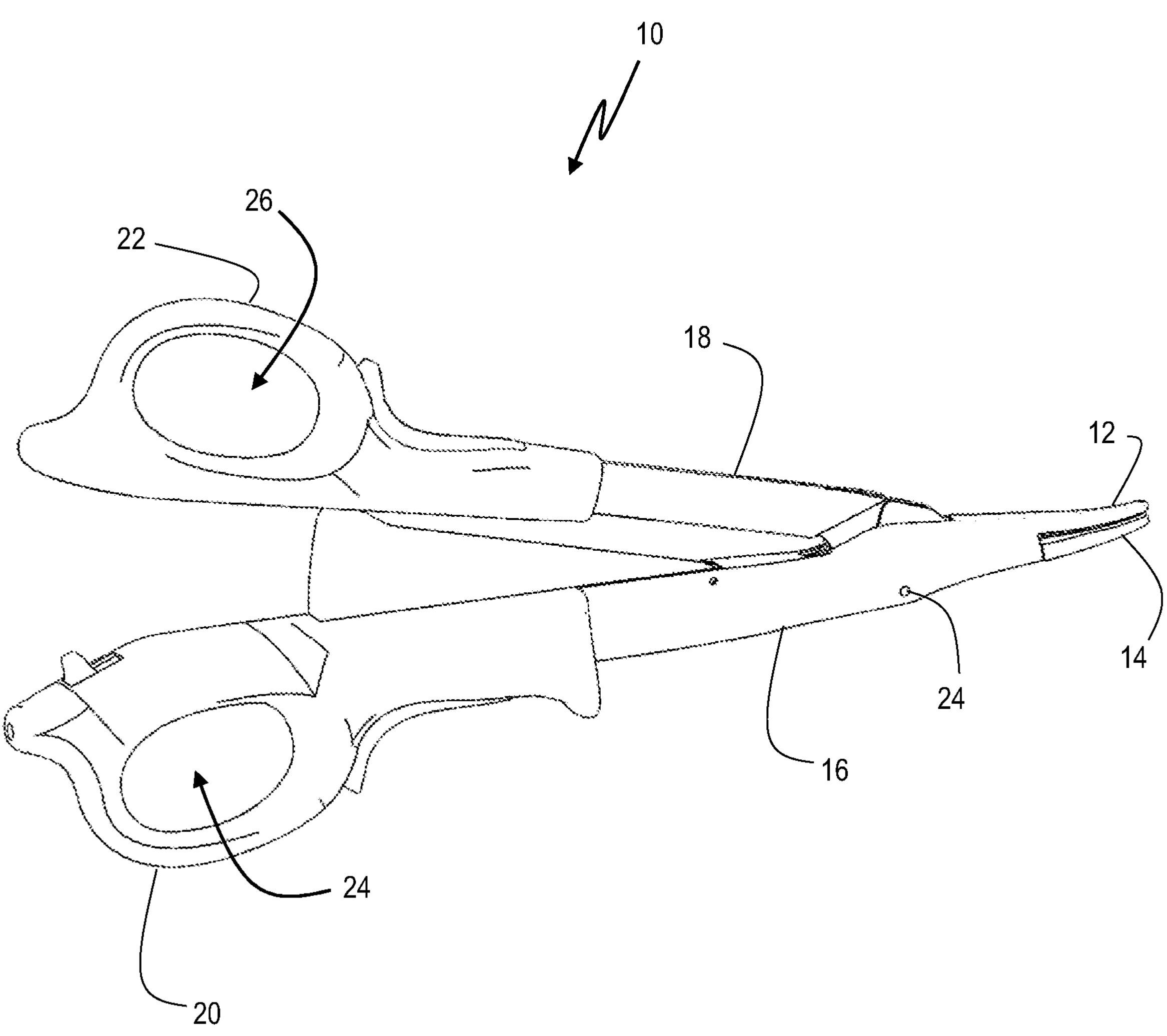
FIG. 2 is a side view of a scissor style vessel sealer having a force limiting mechanism according to the present invention in the jaws closed position.

Referring to the drawings, wherein like numeral refer to like parts throughout, there is seen in FIG. 1 a scissor style vessel sealer 10 according to the present invention. scissor Style vessel sealer 10 comprises a pair of jaws 12 and 14, each of which is mounted to an end of a corresponding shaft 16 and 18. Shafts 16 and 18 are pivotally coupled to each other at an intermediate portion thereof by a pivot 24. The opposing ends of shafts 16 and 18 include user handles 20 and 22 defining finger holes 24 and 26 formed therethrough to allow for easy grasping by a user. As seen in the exemplary orientation of FIG. 1, the upper jaw 12 is connected via shaft 16 to the lower handle 20, and the lower jaw 14 is connected via upper shaft 18 to the upper handle 22. As seen in FIG. 1 and FIG. 2, vessel sealer 10 is operated by driving the user handles 20 and 22 in a scissoring motion to move jaws 12 and 14 from the open position of FIG. 1 to the closed position of FIG. 2, and from the closed position of FIG. 2 back to the open position of FIG. 1. As is known in the art, an electrosurgical generator may be coupled to one or both of jaws 12 and 14 to selectively provide radiofrequency (RF) energy to jaws 12 and 14 to perform electrosurgical operations when jaws 12 and 14 are closed about any tissue to be treated.

Figure 3:
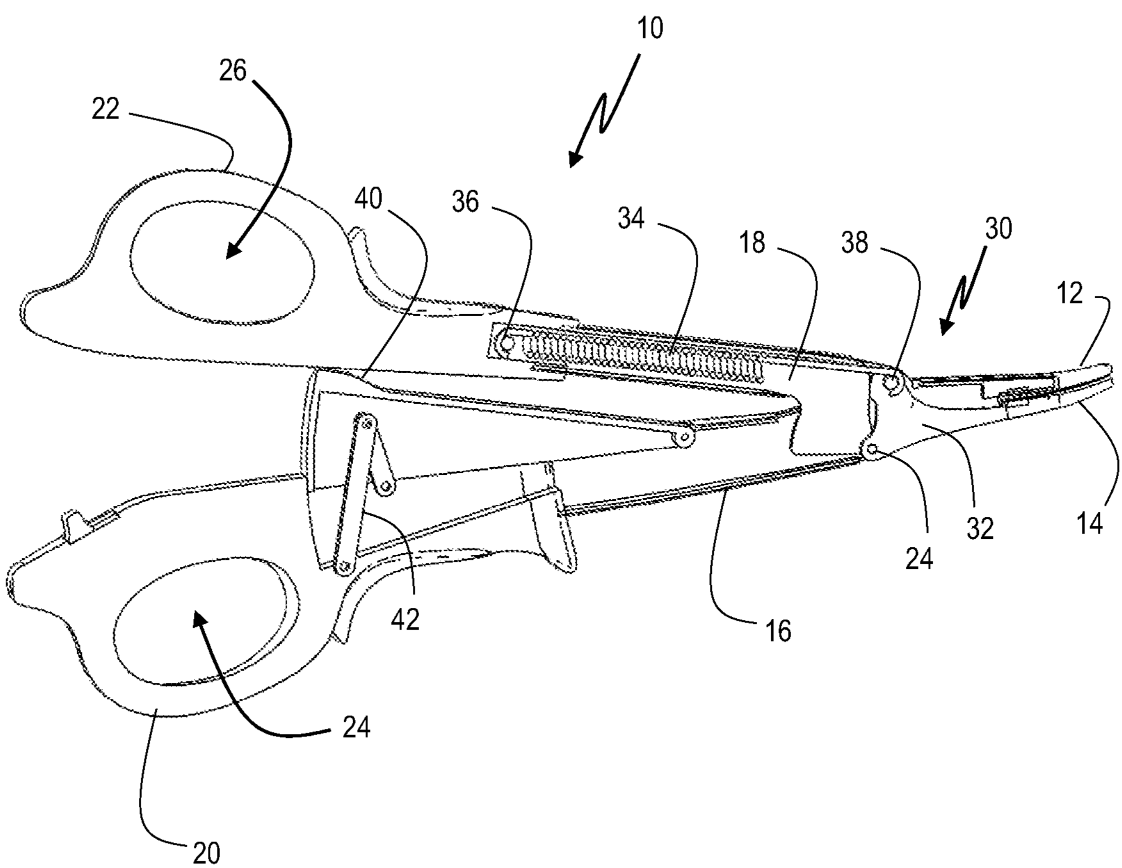
FIG. 3 is a partial section view of a scissor style vessel sealer having a force limiting mechanism according to the present invention in the jaws closed position

Referring to FIG. 3, shaft 18 is indirectly coupled to jaw 14 by a force limiting mechanism 30. More specifically, force limiting mechanism 30 includes a pivot plate 32 that is pivotally interconnects to shaft 18 to jaw 14 about pivot 24 so that when shaft 18 is held in fixed relation to pivot plate 32, shaft 18, pivot plate 32, and jaw 14 will pivot relative to shaft 16 and jaw 12. Pivot plate 32 is additionally interconnected to shaft 18 by a spring 34 that is secured at one end 36 to an intermediate portion of shaft 18 and extends colinearly with shaft 18 and is coupled at an opposing end 38 to pivot plate 32. Spring 34 is attached to pivot plate 38 at a point that is offset from pivot 24 so that spring 34 will provide a predetermined tension to shaft 18 and pivot plate 32 that must be overcome before shaft 18 will be able to pivot about pivot 24 relative to jaw 14. It should be recognized that the amount of offset between pivot 24 and end 38 of spring 34 and the amount of tension of spring 24 can be adjusted to control the amount of force that must be applied to shaft 18 before shaft 18 will be able to pivot about pivot 24 relative to pivot plate 24 and jaw 14, and thus these dimensions and forces can be attenuated to provide a desired amount of force limiting for scissor style vessel sealer 10. Spring 18 can be coupled to shaft 18 and pivot plate 24 via any conventional means including posts, welds, rivets, etc. and could additionally include a slider at end 36 to allow for an adjustment of the amount of force need to overcome the biasing of spring 34.

Figure 4:
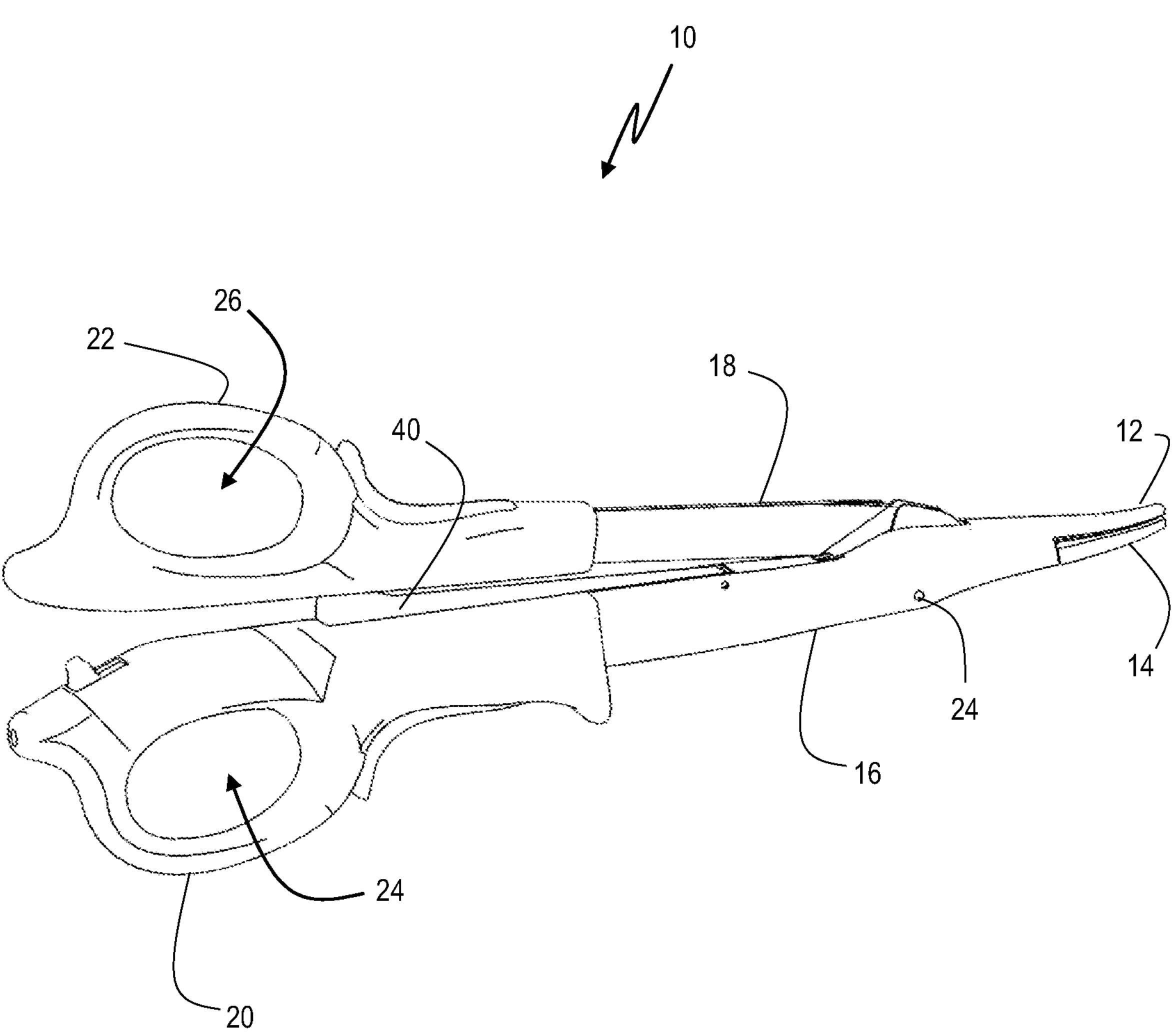
FIG. 4 is a side view of a scissor style vessel sealer having a force limiting mechanism according to the present invention in the jaws closed position and the handles subjected to an overapplication of force.
Figure 5:
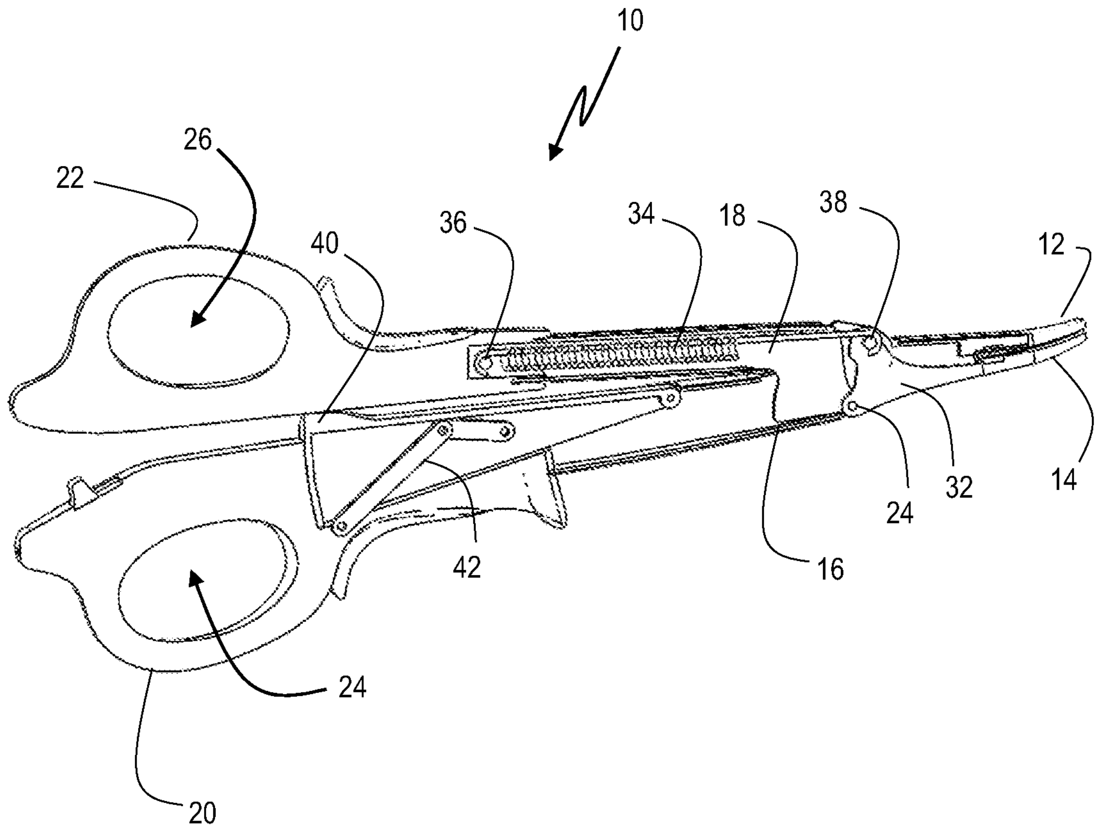
FIG. 5 is a partial section view of a scissor style vessel sealer having a force limiting mechanism according to the present invention in the jaws closed position and the handles subjected to an overapplication of force.

Referring to FIG. 4, the application of any additional scissoring force to scissor style vessel sealer 10 after reaching the jaws closed position will cause pivoting of shaft 18 relative to jaw 14 and thus shaft 18 is free to move beyond the jaws closed position, without applying any appreciable additional force to jaws 12 and 14. Shaft 18 is thus free to continue to move until shaft 18 contacts shaft 16 into a fully scissored position. As seen in FIG. 5, shaft 16 may include a button 40 and linkage 42 that is driven by contact with shaft 18 as it is moved from the jaws fully closed position to the shafts fully scissored position and contacts shaft 16. Force limiting mechanism 30 thus provides for scissoring of scissor style vessel sealer 10 into a third position that is beyond the jaws closed position to prevents the overapplication of force to jaws 12 and 14, and allows a user to cause another mechanical action or event to occur. Button 40 and linkage 42 may be configured to apply user feedback, i.e., to signal to a user that the jaw have been fully closed, and be biased to assist with the manual return of device to the jaws open position. Button 40 and linkage 42 may also be used for additional action. For example, button 40 and linkage 42 may be coupled to drive a knife blade between jaws 12 and 14 to sever any tissue grasped therein. Button 40 and linkage 42 could also be connected to a switch that closes to apply radiofrequency energy to jaws 40 and 42 and thus act as a manual trigger to apply the energy need for coagulation or cutting procedures.

What is claimed is:

1. A scissor style vessel sealer, comprising:

a first shaft interconnected to a first jaw by a pivot plate, where the pivot plate is pivotally coupled to the first shaft and to the first jaw by a pivot and is also coupled to the first shaft by a spring that is secured at one end to the first shaft and at an opposing end to the pivot plate at a location offset from the pivot; and a second shaft connected to a second jaw and pivotally coupled to the first jaw by the pivot of the pivot plate.

2. The scissor style vessel sealer of claim 1, wherein the first shaft and the second shaft are pivotable about the pivot between a first position where the first jaw and the second jaw are open and a second position where the first jaw and the second jaw are closed.

3. The scissor style vessel sealer of claim 2, wherein the first shaft and the second shaft are pivotable about the pivot to a third position where the first jaw and the second jaw are closed and the first shaft has pivoted relative to the first jaw.

4. The scissor style vessel sealer of claim 3, wherein the first shaft is in contact with the second shaft in the third position.

5. The scissor style vessel sealer of claim 3, wherein the second shaft includes a button positioned to be actuated by the first shaft when the first shaft and the second shaft are in the third position.

6. The scissor style vessel sealer of claim 5, wherein the button is coupled to a linkage that provides feedback to a user that the scissor style vessel sealer is in the third position.

7. The scissor style vessel sealer of claim 6, wherein the button is coupled to a switch that triggers energization of the first jaw and the second jaw.

8. The scissor style vessel sealer of claim 5, wherein the linkage can move a knife blade between the first jaw and the second jaw.

9. A scissor style vessel sealer, comprising:

a first shaft interconnected to a first jaw by a pivot;

a second shaft connected to a second jaw and pivotally coupled to the first jaw by the pivot;

wherein the first shaft is free to pivot relative to the first jaw about the pivot in response a predetermined amount of force applied to the first shaft.

10. The scissor style vessel sealer of claim 9, wherein the first shaft and the second shaft are pivotable about the pivot between a first position where the first jaw and the second jaw are open and a second position where the first jaw and the second jaw are closed.

11. The scissor style vessel sealer of claim 10, wherein the first shaft and the second shaft are pivotable about the pivot to a third position where the first jaw and the second jaw are closed and the first shaft has pivoted relative to the first jaw.

12. The scissor style vessel sealer of claim 11, further comprising a spring interconnected between the first shaft and the first jaw that provides a biasing force coupling the first shaft to the first jaw.

13. The scissor style vessel sealer of claim 12, wherein the predetermined amount of force applied to the first shaft will overcome the biasing force of the spring such that the first shaft will pivot about the pivot relative to the first jaw.

14. The scissor style vessel sealer of claim 12, wherein the spring is secured at one end to the first shaft and an opposing end to a pivot plate that is pivotally connected to the first shaft by the pivot.

15. The scissor style vessel sealer of claim 14, wherein the pivot plate is fixed to the first jaw.

16. A method of providing force limiting to a scissor style vessel sealer, comprising the steps of:

providing a first shaft interconnected to a first jaw by a pivot plate that pivotally couples the first shaft to the first jaw by a pivot connecting the first jaw to the pivot plate and also by a spring that is secured at one end to the first shaft and an opposing end to the pivot plate at a location offset from the pivot; and providing a second shaft connected to a second jaw and pivotally coupled to the first jaw by the pivot.

17. The method of claim 16, further comprising the step of applying a force to the first shaft and the second shaft so that the first shaft and the second pivot about the pivot from a first position where the first jaw and the second jaw are open to a second position where the first jaw and the second jaw are closed.

18. The method of claim 17, further comprising the step of continuing to apply the force to the first shaft and the second shaft so that the first shaft pivots relative to the first jaw.

19. The method of claim 18, wherein the pivoting of the first shaft relative to the first jaw causes the first shaft to contact the second shaft.

20. The method of claim 19, wherein the contacting of the first shaft to the second shaft actuates a button.

* * * * *